United States Patent [19]

Maeda et al.

[11] Patent Number: 5,106,866
[45] Date of Patent: Apr. 21, 1992

[54] AMINE DERIVATIVES, PROCESSES FOR PREPARING THE SAME AND FUNGICIDES CONTAINING THE SAME

[75] Inventors: Tetsuya Maeda, Tokorozawa; Toshiyuki Yamamoto, Tokyo; Mituo Takase, Hino; Kazuya Sasaki, Higashikurume; Tadashi Arika, Kasukabe; Mamoru Yokoo, Kawagoe; Rieko Hashimoto, Asaka; Kouji Amemiya, Kodaira; Sakae Koshikawa, Kawaguchi, all of Japan

[73] Assignee: Kaken Pharmaceutical Co., Ltd., Tokyo, Japan

[21] Appl. No.: 479,894

[22] Filed: Feb. 14, 1990

Related U.S. Application Data

[60] Division of Ser. No. 283,055, Dec. 7, 1988, which is a continuation of Ser. No. 73,329, Jul. 13, 1987, abandoned, which is a continuation of Ser. No. 740,596, Jun. 3, 1985, abandoned.

[30] Foreign Application Priority Data

Jun. 9, 1984 [JP] Japan .................. 59-118636

[51] Int. Cl.$^5$ ............... C07D 333/58; A61K 31/38
[52] U.S. Cl. .................. 514/443; 549/49; 549/57; 549/58
[58] Field of Search ............. 549/57, 58, 49; 514/443

[56] References Cited

U.S. PATENT DOCUMENTS 4,684,661 8/1987 Steutz .................. 564/387
4,742,077 5/1988 Stütz .................... 549/58 X

FOREIGN PATENT DOCUMENTS 0000896 3/1979 European Pat. Off. .
2185980 8/1987 United Kingdom .

Primary Examiner—Catherine S. Kilby Scalzo
Attorney, Agent, or Firm—Armstrong, Nikaido, Marmelstein, Kubovcik & Murray

[57] ABSTRACT

Amine derivatives having the general formula (I):

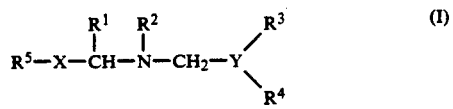

wherein X is selected from the group consisting of

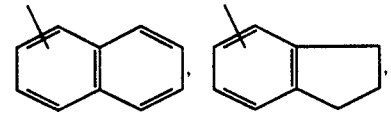

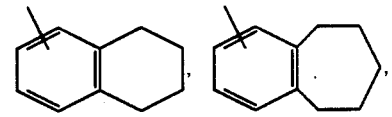

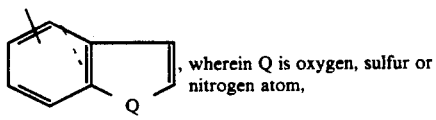

, wherein Q is oxygen, sulfur or nitrogen atom, and

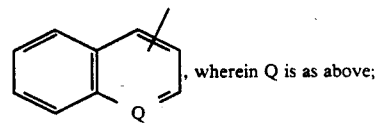

, wherein Q is as above;

Y is selected from the group consisting of

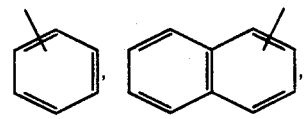

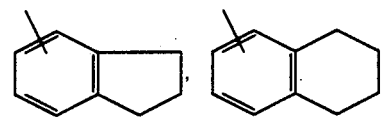

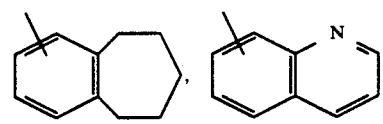

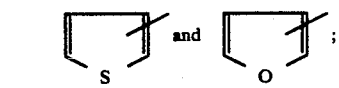

$R^1$ is hydrogen atom or an alkyl group; $R^2$ is hydrogen atom or an alkyl group; $R^3$ is hydrogen atom, a halogen atom or an alkyl group; $R^4$ is hydrogen atom, an alkyl group, a cycloalkyl group, a halogenated alkyl group or a halogen atom; $R^5$ is hydrogen atom, an alkyl group, an alkoxy group, a halogen atom, nitro group or hydroxy group; $R^5$ is attached to an arbitrary position of X, and $R^3$ or $R^4$ is attached to an arbitrary position of Y.

The amine derivatives (I) are useful as fungicides.

2 Claims, No Drawings

AMINE DERIVATIVES, PROCESSES FOR PREPARING THE SAME AND FUNGICIDES CONTAINING THE SAME

This is a division of application Ser. No. 07/283,055 filed Dec. 7, 1988, which is a continuation of application Ser. No. 07/073,329 filed July 13, 1987, now abandoned, which is a continuation of application Ser. No. 06/740,596 filed June 3, 1985, and now abandoned.

BACKGROUND OF THE INVENTION

The present invention relates to novel amine derivatives having the general formula (I):

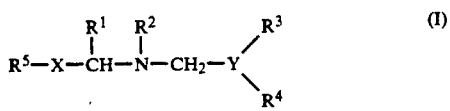

wherein X is selected from the group consisting of

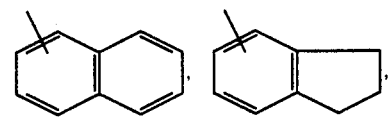

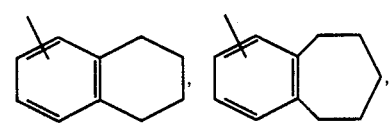

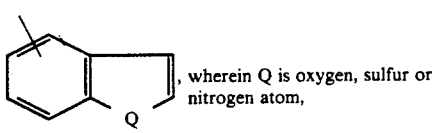, wherein Q is oxygen, sulfur or nitrogen atom, and

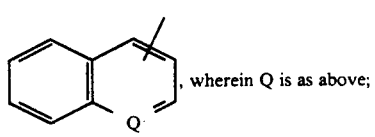, wherein Q is as above;

Y is selected from the group consisting of

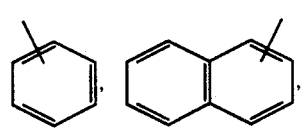

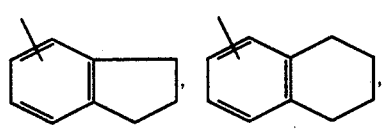

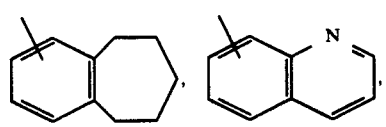

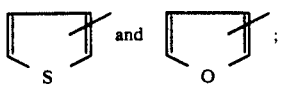

$R^1$ is hydrogen atom or a linear or branched alkyl group having 1 to 6 carbon atoms, preferably having 1 to 4 carbon atoms; $R^2$ is hydrogen atom or linear or branched alkyl group having 1 to 6 carbon atoms, preferably having 1 to 4 carbon atoms; $R^3$ is hydrogen atom, a halogen atom such as fluorine, chlorine, bromine and iodine, or a linear or branched alkyl group having 1 to 6 carbon atoms, preferably having 1 to 4 carbon atoms; $R^4$ is hydrogen atom, a linear or branched alkyl group having 1 to 10 carbon atoms, preferably having 1 to 7 carbon atoms, cycloalkyl group having 3 to 7 carbon atoms, preferably having 5 to 6 carbon atoms, halogenated alkyl group such as trifluoro methyl group, or a halogen atom such as fluorine, chlorine, bromine and iodine; $R^5$ is hydrogen atom, a linear or branched alkyl group having 1 to 6 carbon atoms, preferably having 1 to 4 carbon atoms, a linear or branched alkoxy group having 1 to 6 carbon atoms, preferably having 1 to 4 carbon atoms, a halogen atom such as fluorine, chlorine, bromine and iodine, nitro group or hydroxy group; $R^5$ is attached to an arbitrary position of X, and $R^3$ or $R^4$ is attached to an arbitrary position of Y, processes for preparing the same and fungicides containing the same as an effective component.

The acid addition salts of said amine derivatives having general formula (I) are, for instance, hydrochloride, hydrobromide, sulfate, nitrate, acetate, oxalate, tartrate, benzenesulfate, methanesulfate and the like, which are pharmacologically acceptable.

The compounds according to the present invention can be prepared, for instance, by the process (a) which comprises reacting the compound having the general formula (II):

wherein $R^1$, $R^5$ and X are as above, A is an eliminating group or $R^2$—NH—, wherein $R^2$ is as above, with the compound having the general formula (III):

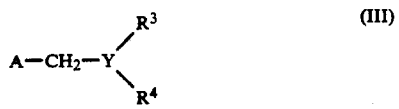

wherein $R^3$, $R^4$ and Y are as above, A is an eliminating group or 2—NH—, wherein $R^2$ is as above, and A is different from that of formula (II) or the process (b) which comprises reducing the compound having the general formula (IV):

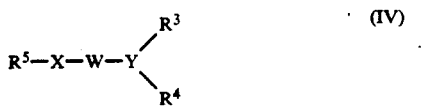

wherein $R^3$, $R^4$, $R^5$, X and Y are as above, W is $$-CH-N-CO-,$$
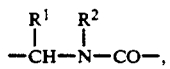

wherein $R^1$ and $R^2$ are as above, and by collecting the obtained product from the process (a) or the process (b) in the form of a free base or an acid addition salt.

The above-mentioned processes (a) and (b) can be carried out in the conventional manner.

The process (a) can be carried out in the reaction solvent of aromatic hydrocarbon such as benzene and toluene, ether such as diethyl ether and dioxane, or carboxylic acid alkyl amide such as dimethylformamide at a reaction temperature ranging from room temperature to a boiling point of the solvent, preferably from room temperature to 60° C. Examples of eliminating group A are a halogen atom such as chlorine and bromine, organic sulfonyloxy group having 1 to 10 carbon atoms such as tosyloxy and mesyloxy. The reaction is advantageously carried out in the presence of reagent binding with acid, i.e. hydroxide of alkali metal or alkaline earth metal, or carbonate of alkali metal or alkaline earth metal such as sodium carbonate and potassium carbonate.

The process (b) can be carried out in an inactive solvent of ether such as diethyl ether, tetrahydrofuran and dioxane at room temperature or a reaction temperature ranging from room temperature to a boiling point of the solvent, using lithium aluminum hydride as a reducing agent.

The reaction to convert the compound of the present invention having the general formula (I) from its free base into its acid addition salt, or from its acid addition salt into its free base, can be carried out in the conventional manner.

The compounds having the general formula (II), (III) or (IV) which are the starting materials and used for preparing the compound of the present invention having the general formula (I) can be produced easily in the conventional manner whether or not they are known or novel compounds. Examples of preparing them are as follows:

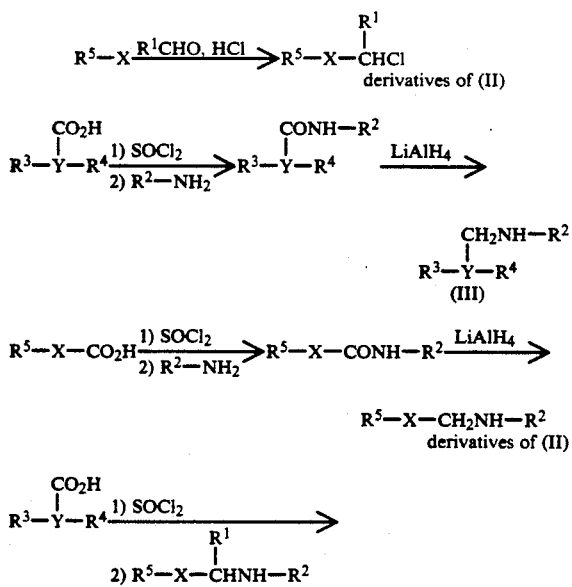

-continued
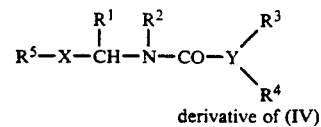

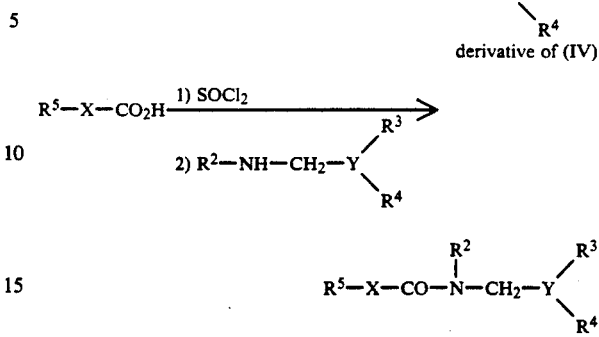

wherein $R^1$, $R^2$, $R^3$, $R^4$, $R^5$, X and Y are as above.

The reaction may be carried out under such conditions as usually employed in such reaction and various intermediates can be subjected to further reaction without isolation. In case that isolation is necessary, it can be carried out by the conventional process.

The compounds of the present invention show an excellent antifungal activity. They show an antifungal activity at the concentration of 0.003 to 100 μg/ml in vitro especially against such fungi as Trichophyton mentagrophytes, Trichophyton interdigitale, Trichophyton rubrum, Microsporum canis, Microsporum gypseum, Epidermophyton floccosum, Cryptococcuss neoformans, Sporothrix schenekii, Aspergillus fumigatus and Candida albicans. In vivo test of dermatomycosis model employing guinea pig (see Sumio Sakai: Shinkin To Shinkinsho, vol. 1, page 252, 1960) also ascertained that the compounds of the present invention have an excellent antifungal activity.

The compounds of the present invention can provide fungicides in the form of liquid preparation, ointment, cream and the like. Though an amount of an effective component may vary depending on species of fungi, a degree of desease, a kind of the compound employed, dosage form, and the like, generally the compounds of the present invention can provide fungicides at a concentration of 0.01 to 5%.

The present invention is further explained by the following Reference Examples, Examples, Preparation Examples and Test Examples. However, it is to be understood that the present invention is not limited to these Examples and various changes and modifications may be made without departing from the spirit of the present invention.

The following NMR spectrum is shown in value measured in CDCl₃ employing TMS as standards.

Melting points in each Example are those of hydrochloride of the compound and NMR spectrum are those of freebase of the compound.

REFERENCE EXAMPLE 1 [Preparation of 4-iodo-1-chloromethylnaphthalene]

A mixture of 17.8 g of 1-iodo-naphthalene, 4.4 g of paraformaldehyde, 10.4 ml of acetic acid, 14.6 ml of concentrated hydrochloric acid and 6.6 ml of phosphoric acid was stirred at 80° to 85° C. and thereto another 20 ml of concentrated hydrochloric acid was added with stirring 8 times at intervals of 1 hour. The reaction mixture was poured into water and was extracted with benzene. After distilling away benzene, 18.5 g of 4-iodo-1-chloromethylnaphthalene was obtained.

Nuclear magnetic resonance spectrum δ (CDCl$_3$)
8.08 to 6.86 (m, 6H) and 4.78 (s, 2H)

The following compound was also prepared by the same procedures.

4-Bromo-1-chloromethylnaphthalene
Melting point: 82° to 83.5° C.

Nuclear magnetic resonance spectrum δ (CDCl$_3$): 8.33 to 7.15 (m, 6H) and 4.86 (s, 2H)

REFERENCE EXAMPLE 2

Preparation of N-methyl-4-tert-butylbenzylamine

A mixture of 178 g of 4-tert-Butyl benzoic acid and 360 g of thionyl chloride was stirred at 50° C. for 5 hours. After distilling away an excess of thionyl chloride under reduced pressure, the resultant was added dropwise to 300 ml of 40% aqueous solution of methylamine and the resultant mixture was stirred for 3 hours. Acidification with hydrochloric acid precipitated 171 g of N-methyl-4-tert-butyl benzamide (melting point: 99° to 100° C.).

To a mixture of 30.4 g of lithium aluminum hydride and 1 l of anhydrous diethyl ether was added the obtained amide and the reaction mixture was refluxed for 6 hours. After cooling, an excess of lithium aluminum hydride was decomposed by adding dropwise of water and the ether layer was separated. The ether solution was washed with water and dried over anhydrous solution sulfate. After distilling away ether, colourless liquid of N-methyl-4-tert-butylbenzylamine (boiling point: 93° to 95° C./6 mmHg) was obtained by distillation under reduced pressure.

Nuclear magnetic resonance spectrum δ (CDCl$_3$):
7.26 (s, 4H), 3.68 (s, 2H), 2.42 (s, 3H) and 1.29 (s, 9H)
Melting point of hydrochloride: 208.5° to 209.5° C.

REFERENCE EXAMPLE 3

Preparation of N-propyl-1-naphthylmethylamine

To 116 g of propylamine was added dropwise 25 g of 1-naphthoyl chloride and the resultant mixture was stirred for 3 hours. Then the crystal formed by acidification with hydrochloric acid was filtrated and was washed with water. Obtained 26.8 g of N-propyl-1-naphthamide was added to a mixture of 14.1 g of lithium aluminum hydride and 300 ml of anhydrous diethyl ether and the reaction mixture was refluxed for 11 hours. After cooling, an excess of lithium aluminum hydride was decomposed by adding dropwise of water and the ether layer was separated. After distilling away ether, 16.6 g of N-propyl-1-naphthylmethylamine (boiling point: 133° to 134° C./1.5 mmHg) was obtained as colourless liquid by distillation under reduced pressure.

Nuclear magnetic resonance spectrum δ (CDCl$_3$): 8.2 to 7.2 (m, 7H), 4.20 (s, 2H), 2.69 (t, J=7Hz, 2H), 1.86 to 1.15 (m, 2H) and 0.90 (t, J=7Hz, 3H)

The following compounds were also prepared by the same procedures.

N-Methyl-1-naphthylmethylamine
N-Ethyl-1-naphthylmethylamine
N-Butyl-1-naphthylmethylamine

REFERENCE EXAMPLE 4

Preparation of N-methyl-N-(1-naphthylmethyl)-4-isopropyl benzamide

A mixture of 0.99 g of 4-isopropyl benzoic acid and 3.6 g of thionyl chloride was stirred at 50° C. for 4 hours and then an excess of thionyl chloride was removed under reduced pressure. Obtained acid chloride was dissolved into 5 ml of anhydrous benzene and the solution was added dropwise to mixture of 1.03 g of N-methyl-1-naphthylmethylamine, 2 ml of triethylamine and 15 ml of anhydrous benzene and the resultant was stirred for 3 hours. The mixture was then poured into water, extracted with benzene and washed successively with 5% aqueous solution of hydrochloric acid, 3% aqueous solution of sodium bicarbonate and water. After distilling away benzene, viscous N-methyl-N-(1-naphthylmethyl)-4-isopropylbenzamide was obtained.

Nuclear magnetic resonance spectrum δ (CCl$_4$, TMS standard): 8.0 to 7.0 (m, 11H), 5.03 (s, 2H), 2.80 (s, 3H), 3.1 to 2.6 (m, 1H) and 1.18 (s, J=7Hz, 6H)

The following compounds were also prepared by the same procedures.

N-Methyl-N-(1-naphthylmethyl)-4-ethylbenzamide
Nuclear magnetic resonance spectrum δ (CCl$_4$, TMS standard): 8.0 to 6.95 (m, 11H), 5.07 (s, 2H), 2.78 (s, 3H), 2.75 (q, J=7.6Hz, 2H) and 1.15 (t, J=7.6Hz, 2H)

N-Methyl-N-(1-naphthylmethyl)-4-butylbenzamide
Nuclear magnetic resonance spectrum δ (CCl$_4$, TMS standard): 8.0 to 6.9 (m, 11H), 5.02 (s, 2H), 2.79 (s, 3H), 2.79 (s, 3H), 2.54 (t, J=7Hz, 2H), 1.7 to 1.15 (m, 4H) and 0.88 (t, J=7Hz, 3H)

N-Methyl-N-(1-naphthylmethyl)-3,4-dimethylbenzamide
Nuclear magnetic resonance spectrum δ (CCl$_4$, TMS standard): 8.0 to 6.8 (m, 10H), 4.99 (s, 2H), 2.76 (s, 3H) and 2.13 (s, 6H)

N-Methyl-N-(1-naphthylmethyl)-3,5-dimethylbenzamide
Nuclear magnetic resonance spectrum δ (CCl$_4$, TMS standard): 8.0 to 6.8 (m, 10H), 5.00 (s, 2H), 2.72 (s, 3H) and 2.15 (s, 6H)

N-Methyl-N-(1-naphthylmethyl)-4-iodobenzamide
Melting point: 136.5° to 138.5° C.
Nuclear magnetic resonance spectrum δ (CCl$_4$, TMS standard): 8.0 to 7.01 (m, 11H), 5.03 (s, 2H) and 2.80 (s, 3H)

REFERENCE EXAMPLE 5

Preparation of N-(4-tert-buthylbenzyl)-N-methyl-2-ethoxycarboxy-1-naphthamide

Into an aqueous solution of sodium hydroxide (3.63 g of sodium hydroxide and 71.5 ml of water) was dissolved 7.52 g of 2-hydroxy-1-naphthoic acid and thereto 9.59 g of ethyl chloroformate was added dropwise at cooling. After the mixture was stirred at room temperature for 1 hour, it was poured into water, extracted with benzene, washed with water and dried over anhydrous sodium sulfate. Sodium sulfate was removed and then 5.24 g of thionyl chloride was added. The reaction was carried out at 40° C. for 3 hours and the obtained acid chloride was added dropwise to a mixture of 7.08 g of N-methyl-4-tert-benzylamine and 8 g of pyridine and then stirred for 3 hours. The reaction mixture was poured into water, extracted with benzene, and the benzene solution was washed successively with 3% aqueous solution of hydrochloric acid, subsequently with water, and dried over anhydrous sodium sulfate. After distilling away benzene, 6.6 g of oily N-(4-tert-butylbenzyl)-methyl-2-ethoxycarboxy-1-naphthamide was obtained.

EXAMPLE 1

A mixture of 1.94 g of 1-chloromethylnaphthalene, 1.77 g of N-methyl-4-tert-butylbenzylamine, 1.17 g of sodium carbonate and 10 ml of dimethylformamide was stirred for 14 hours at 50° C. The reaction mixture was poured into water and extracted with benzene, and the benzene solution was washed with water. After distillig away benzene, 1.5 ml of concentrated hydrochloric acid was added, an excess of concentrated hydrochloric acid was removed under reduced pressure, a small amount of acetone was added and formed white crystal (2.75 g) was filtrated. White plate crystal of N-(4-tert-butylbenzyl)-N-methyl-1-naphthylmethylamine hydrochloride was obtained by recrystallization from acetone/ethanol.

Melting point: 211° to 213° C.

Nuclear magnetic resonance spectrum δ: 8.3 to 7.3 (m, 11H), 3.91 (s, 2H), 3.56 (s, 2H), 2.19 (s, 3H) and 1.33 (s, 9H)

Mass spectrum (m/e): 317 (M+), 190, 176, 170, 147 and 141 (base)

EXAMPLE 4

N-4-tert-Butylbenzyl-N-methyl-4-fluoro-1-naphthamide (2.0 g) was obtained by the reaction of 1.23 g of 1-Chloromethyl-4-fluoronaphthalene and 1.15 g of N-Methyl-4-tert-butylbenzylamine.

EXAMPLE 9

N-4-tert-Butylbenzyl-N-methyl-1-(1-naphthyl)ethylamine (1.33 g) was obtained by the reaction of 1.20 g of 1-(1-Chloroethyl)naphthalene and 1.15 g of N-Methyl-4-tert-butylbenzylamine.

EXAMPLE 12

N-Methyl-N-4-tert-pentylbenzyl-1-naphthylmethylamine (1.65 g) was obtained by the reaction of 1.11 g of 1-Chloromethylnaphthalene and 1.15 g of N-Methyl-4-tert-pentylbenzylamine.

EXAMPLE 22

N-4-Isopropylbenzyl-N-methyl-1-naphthylmethylamine (1.47 g) was obtained by the reaction of 1.11 g of 1-Chloromethylnaphthalene and 0.98 g of N-Methyl-4-isopropylbenzylamine.

EXAMPLE 29

N-4-tert-Butylbenzyl-N-methyl-3-benzo[b]thienylmethylamine (1.4 g) was obtained by the reaction of 0.89 g of 3-Chloromethylbenzo[b]thiophene and 0.91 g of N-Methyl-4-tert-butylbenzylamine.

EXAMPLES 2 to 71

The procedures of Example 1 were repeated to give hydrochlorides of various amine derivatives. Melting points of each compounds are shown in Table 1.

TABLE 1

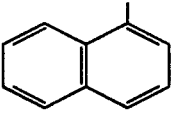

| No. | —X—R$^5$ | R$^1$ | R$^2$ | $-Y\begin{smallmatrix}R^3\\R^4\end{smallmatrix}$ | Melting point (°C.) |
|---|---|---|---|---|---|
| 1 | 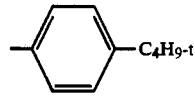 | H | CH$_3$ | 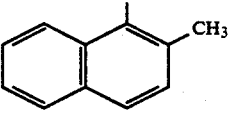 | 211 to 213 |
| 2 | 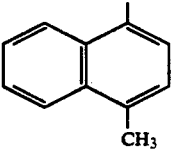 | " | " | " | 218 to 220 |
| 3 | 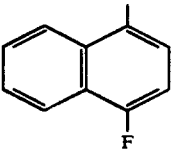 | " | " | " | 231 to 233 |
| 4 |  | " | " | " | 237 to 239 |

TABLE 1-continued $$R^5-X-\underset{\underset{R^1}{|}}{CH}-\underset{}{N}-CH_2-Y\underset{R^4}{\overset{R^3}{<}}$$

| No. | —X—R⁵ | R¹ | R² | $-Y<^{R^3}_{R^4}$ | Melting point (°C.) |
|---|---|---|---|---|---|
| 5 | 1-chloronaphthyl (Cl at 4-position) | " | " | " | 236 to 238 |
| 6 | 1-bromonaphthyl (Br at 4-position) | " | " | " | 240 to 242 |
| 7 | 1-iodonaphthyl (I at 4-position) | H | CH₃ | —C₆H₄—C₄H₉-t (para) | 225 to 227 |
| 8 | 1-nitronaphthyl (NO₂ at 4-position) | " | " | " | 223 to 225 |
| 9 | naphthyl | CH₃ | " | " | 222 to 224 |
| 10 | 2-naphthyl | H | " | " | 228.5 to 230.5 |
| 11 | 2-methoxy-1-naphthyl (OCH₃) | " | " | " | 196 to 198 |
| 12 | 1-naphthyl | " | " | —C₆H₄—C₅H₁₁-t (para) | 191 to 193 |
| 13 | " | " | " | —C₆H₄—CH₃ (meta) | 213 to 214 |

TABLE 1-continued $$R^5-X-\underset{\underset{R^1}{|}}{CH}-\underset{\underset{R^2}{|}}{N}-CH_2-Y\underset{R^4}{\overset{R^3}{<}}$$

| No. | —X—R⁵ | R¹ | R² | $-Y\overset{R^3}{\underset{R^4}{<}}$ | Melting point (°C.) |
|---|---|---|---|---|---|
| 14 | 1-methylnaphthyl | H | CH₃ | 3-CF₃-phenyl | 197 to 199 |
| 15 | " | " | " | 4-CH₃-phenyl | 192 to 194 |
| 16 | " | " | " | 4-cyclohexyl-phenyl | 205 to 207 |
| 17 | " | " | " | 3,4-diCl-phenyl | 211 to 212.5 |
| 18 | " | " | C₂H₅ | 4-C₄H₉-t-phenyl | 190 to 195 |
| 19 | " | " | C₃H₇ | " | 174 to 176.5 |
| 20 | " | " | C₄H₉ | " | 165 to 170 |
| 21 | 1-methylnaphthyl | H | CH₃ | 4-Br-phenyl | 211 to 213 |
| 22 | " | " | " | 4-C₃H₇-i-phenyl | 195.5 to 197 |
| 23 | " | " | " | 4-C₂H₅-phenyl | 202 to 203.5 |
| 24 | " | " | " | 4-C₄H₉-phenyl | 190 to 191 |
| 25 | " | " | " | 2,4-diCH₃-phenyl | 197.5 to 199 |

TABLE 1-continued
$$R^5-X-\overset{R^1}{\underset{}{CH}}-\overset{R^2}{\underset{}{N}}-CH_2-Y\overset{R^3}{\underset{R^4}{\diagdown}}$$
| No. | —X—R⁵ | R¹ | R² | $-Y\diagup^{R^3}_{R^4}$ | Melting point (°C.) |
|---|---|---|---|---|---|
| 26 | " | " | " | 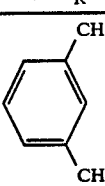 | 188 to 189 |
| 27 | " | " | " | 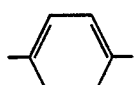 | 215 to 217 |
| 28 | 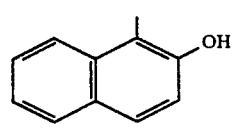 | H | CH₃ | 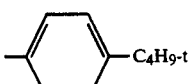 | 181 to 183 |
| 29 | 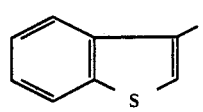 | " | " | " | 216 to 217.5 |
| 30 | " | " | C₂H₅ | " | 173 to 175 |
| 31 | " | " | CH₃ | 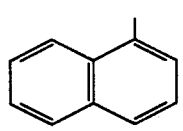 | 223 to 224 |
| 32 | " | " | " | 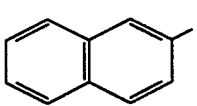 | 237 to 238 |
| 33 | 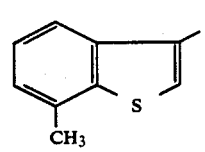 | " | " | 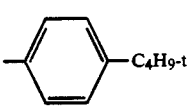 | 219 to 221 |
| 34 | 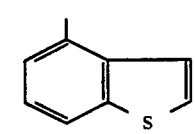 | " | " | " | 219 to 221 |
| 35 | 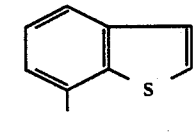 | " | " | 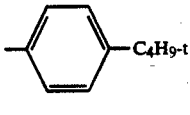 | |
| 36 | 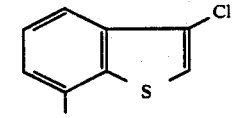 | " | " | " | |

TABLE 1-continued $$R^5-X-\overset{R^1}{\underset{CH}{|}}-\overset{R^2}{\underset{N}{|}}-CH_2-Y\overset{R^3}{\underset{R^4}{\diagup}}$$

| No. | —X—R⁵ | R¹ | R² | —Y$\diagup_{R^4}^{R^3}$ | Melting point (°C.) |
|---|---|---|---|---|---|
| 37 | [3-bromobenzothiophen-2-yl] | " | " | " | 220 to 221.5 |
| 38 | [indan-5-yl] | " | " | " | 210 to 212 (dec) |
| 39 | [5,6,7,8-tetrahydronaphthalen-1-yl] | " | " | " | 189.5 to 190.5 |
| 40 | [5,6,7,8-tetrahydronaphthalen-2-yl] | " | " | " | 237 to 238 |
| 41 | [4-fluoronaphthalen-1-yl] | " | " | " | 232.5 to 233 (dec) |
| 42 | [4-fluoronaphthalen-1-yl] | H | CH₃ | [4-tert-butylphenyl] | 237 to 239 |
| 43 | " | " | " | [naphthalen-2-yl] | 243 to 243.5 |
| 44 | [4-chloronaphthalen-1-yl] | " | " | [naphthalen-1-yl] | 233 to 234 |
| 45 | " | " | " | [naphthalen-2-yl] | 247 to 249 |

TABLE 1-continued
$$R^5-X-\underset{\underset{R^1}{|}}{CH}-\underset{\underset{R^2}{|}}{N}-CH_2-Y\underset{R^4}{\overset{R^3}{\diagup}}$$
| No. | —X—R⁵ | R¹ | R² | —Y$\diagdown\!\!\!\diagup\overset{R^3}{\underset{R^4}{}}$ | Melting point (°C.) |
|---|---|---|---|---|---|
| 46 | 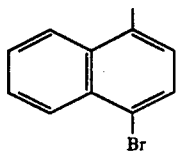 | " | " | 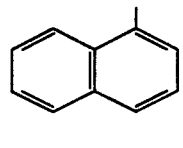 | 228 to 228.5 |
| 47 | " | " | " | 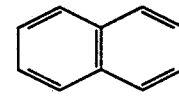 | 235.5 to 236.5 |
| 48 | 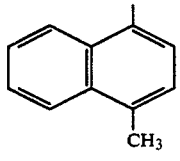 | H | CH₃ | 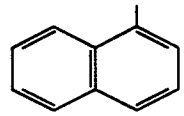 | 219 to 220 |
| 49 | 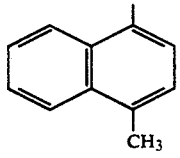 | " | " | 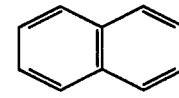 | 238 to 239 |
| 50 | 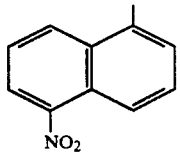 | " | " | " | 233 to 236 |
| 51 | 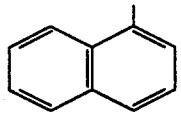 | CH₃ | " | " | 215 to 217 |
| 52 | " | H | " | 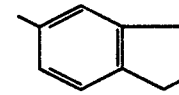 | 192 to 194 |
| 53 | " | " | " | 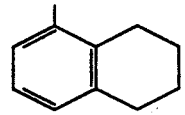 | 126 to 128 (dec) |
| 54 | 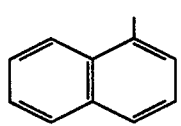 | H | CH₃ | 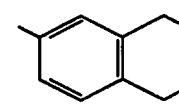 | 197 to 200 |

TABLE 1-continued
$$R^5-X-\overset{R^1}{\underset{}{C}}H-\overset{R^2}{\underset{}{N}}-CH_2-Y\overset{R^3}{\underset{R^4}{\diagdown}}$$
| No. | −X−R⁵ | R¹ | R² | $-Y\overset{R^3}{\underset{R^4}{\diagdown}}$ | Melting point (°C.) |
|---|---|---|---|---|---|
| 55 | " | " | C₂H₅ | 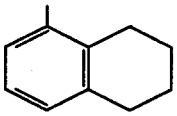 | 194 to 196 |
| 56 | " | " | " | 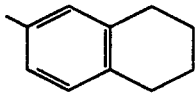 | 174 to 179 |
| 57 | " | " | C₃H₇ | 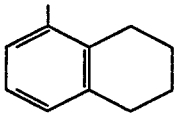 | 163 to 169 |
| 58 | " | " | " | 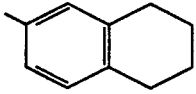 | 183 to 186 |
| 59 | " | " | C₄H₉ | 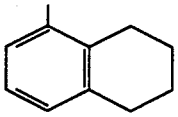 | 173 to 176 |
| 60 | " | " | " | 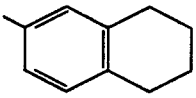 | |
| 61 | 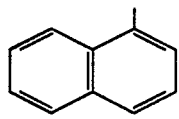 | H | CH₃ | 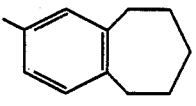 | |
| 62 | " | " | C₂H₅ | 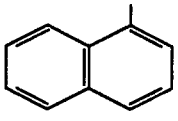 | 214 to 215 |
| 63 | " | " | " | 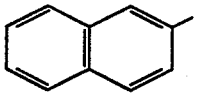 | 194 to 195 |
| 64 | " | " | C₃H₇ | 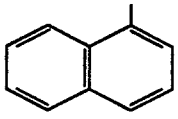 | 193 to 194 |
| 65 | " | " | " | 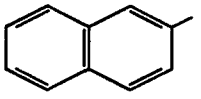 | 206 to 208.5 |

TABLE 1-continued $$R^5-X-\underset{\underset{H}{|}}{\overset{\overset{R^1}{|}}{C}}H-\underset{\underset{H}{|}}{\overset{\overset{R^2}{|}}{N}}-CH_2-Y\overset{R^3}{\underset{R^4}{\diagdown}}$$

| No. | —X—R⁵ | R¹ | R² | $-Y\diagup^{R^3}_{\diagdown R^4}$ | Melting point (°C.) |
|---|---|---|---|---|---|
| 66 | " | " | C₄H₉ | 1-naphthyl | 156 to 158 |
| 67 | " | " | " | 2-naphthyl | 177 to 179 |
| 68 | 1-naphthyl | H | CH₃ | 2-quinolyl | 102 to 103 (base) |
| 69 | " | " | " | 5-(t-C₄H₉)-2-thienyl | 199 to 201.5 |
| 70 | " | " | H | 4-(t-C₄H₉)-phenyl | 203 to 208 |
| 71 | 4-quinolyl | " | CH₃ | " | |

The followings are NMR and MS (m/e) data of each compound of Examples 2 to 71.

EXAMPLE 2

Nuclear magnetic resonance spectrum δ: 8.35 to 7.23 (m, 10H), 3.97 (s, 2H), 3.54 (s, 2H), 2.57 (s, 3H), 2.17 (s, 3H) and 1.28 (s, 9H)

Mass spectrum (m/e): 331 (M+), 176, 152 (base) and 147

EXAMPLE 3

Nuclear magnetic resonance spectrum δ: 8.4 to 7.3 (m, 10H), 3.88 (s, 2H), 3.53 (s, 2H), 2.63 (s, 3H), 2.13 (s, 3H) and 1.28 (s, 9H)

Mass spectrum (m/e): 331 (M+), 184, 176, 152 (base) and 147

EXAMPLE 4

Nuclear magnetic resonance spectrum δ: 8.3 to 6.8 (m, 10H), 3.84 (s, 2H), 3.52 (s, 2H), 2.18 (s, 3H) and 1.30 (s, 9H)

Mass spectrum (m/e): 335 (M+), 188, 176, 154 (base) and 147

EXAMPLE 5

Nuclear magnetic resonance spectrum δ: 8.3 to 7.3 (m, 10H), 3.83 (s, 2H), 3.53 (s, 2H), 2.17 (s, 3H) and 1.30 (s, 9H)

Mass spectrum (m/e): 351 (M+), 204, 176, 175 (base) and 147

EXAMPLE 6

Nuclear magnetic resonance spectrum δ: 8.3 to 7.3 (m, 10H), 3.77 (s, 2H), 3.50 (s, 2H), 2.13 (s, 3H) and 1.29 (s, 9H)

Mass spectrum (m/e): 397 (M+), 395 (M+), 250, 248, 219, 201, 176 (base) and 147

EXAMPLE 7

Nuclear magnetic resonance spectrum δ: 8.3 to 7.1 (m, 10H), 3.82 (s, 2H), 3.52 (s, 2H), 2.17 (s, 3H) and 1.30 (s, 9H)

Mass spectrum (m/e): 443 (M+), 296, 267, 217, 176 (base) and 147

EXAMPLE 8

Nuclear magnetic resonance spectrum δ: 8.6 to 7.3 (m, 10H), 3.91 (s, 2H), 3.54 (s, 2H), 2.19 (s, 3H) and 1.29 (s, 9H)

Mass spectrum (m/e): 362 (M+), 215, 186, 176 and 147 (base)

EXAMPLE 9

Nuclear magnetic resonance spectrum δ: 8.54 to 7.22 (m, 11H), 4.36 (q, J=6.6Hz, 1H), 3.63 (d, J=13Hz, 1H), 3.34 (d, J=13Hz, 1H), 2.19 (s, 3H), 1.53 (d, J=6.6Hz, 2H) and 1.28 (s, 9H)

Mass spectrum (m/e): 331 (M+), 316, 204, 176, 152 and 147 (base)

EXAMPLE 10

Nuclear magnetic resonance spectrum δ: 7.9 to 7.3 (m, 11H), 3.63 (s, 2H), 3.53 (s, 2H), 2.21 (s, 3H) and 1.31 (s, 9H)

Mass spectrum (m/e): 317 (M+), 176 (base), 170, 147, 142 and 141

EXAMPLE 11

Nuclear magnetic resonance spectrum δ: 8.3 to 7.1 (m, 10H), 3.98 (s, 2H), 3.88 (s, 3H), 3.55 (s, 2H) 2.20 (s, 3H) and 1.28 (s, 9H)

Mass spectrum (m/e): 347 (M+), 200, 176, 171 (base), 147 and 141

EXAMPLE 12

Nuclear magnetic resonance spectrum δ: 8.3 to 7.3 (m, 11H), 3.88 (s, 2H), 3.54 (s, 2H), 2.17 (s, 3H), 1.61 (q, J=7.3Hz, 2H), 1.26 (s, 6H) and 0.67 (t, J=7.3Hz, 3H)

Mass spectrum (m/e): 331 (M+), 190, 170, 155 and 141 (base)

EXAMPLE 13

Nuclear magnetic resonance spectrum δ: 8.3 to 7.1 (m, 11H), 3.90 (s, 2H), 4.55 (s, 2H), 2.33 (s, 3H) and 2.19 (s, 3H)

Mass spectrum (m/e): 275 (M+), 170, 141 (base), 134 and 105

EXAMPLE 14

Nuclear magnetic resonance spectrum δ: 8.3 to 7.3 (m, 11H), 3.87 (s, 2H), 3.53 (s, 2H) and 2.16 (s, 3H)

Mass spectrum (m/e): 329 (M+), 202, 188, 154, 142 and 141 (base)

EXAMPLE 15

Nuclear magnetic resonance spectrum δ: 8.3 to 7.0 (m, 11H), 3.87 (s, 2H), 3.53 (s, 2H), 2.29 (s, 3H) and 2.15 (s, 3H)

Mass spectrum (m/e): 275 (M+), 170, 141 (base), 134 and 115

EXAMPLE 16

Nuclear magnetic resonance spectrum δ: 8.3 to 7.0 (m, 11H), 3.89 (s, 2H), 3.54 (s, 2H), 2.5 (m, 1H), 2.17 (s, 3H) and 2 to 1.1 (m, 10H)

Mass spectrum (m/e): 343 (M+), 202, 173, 170 and 141 (base)

EXAMPLE 17

Nuclear magnetic resonance spectrum δ: 8.3 to 7.0 (m, 10H), 3.87 (s, 2H), 3.43 (s, 2H) and 2.15 (s, 3H)

Mass spectrum (m/e): 329 (M+), 202, 188, 170, 142 and 141 (base)

EXAMPLE 18

Nuclear magnetic resonance spectrum δ: 8.3 to 7.2 (m, 11H), 3.97 (s, 2H), 3.54 (s, 2H), 2.56 (q, J=7Hz, 2H), 1.24 (s, 9H) and 1.02 (t, J=7Hz, 3H)

Mass spectrum (m/e): 331 (M+), 316, 190, 147 and 141 (base)

EXAMPLE 19

Nuclear magnetic resonance spectrum δ: 8.3 to 7.2 (m, 11H), 3.91 (s, 2H), 3.53 (s, 2H), 2.59 (t, J=7Hz, 2H), 1.74 to 1.47 (m, 2H), 1.25 (s, 9H) and 0.78 (t, J=7Hz, 3H)

Mass spectrum (m/e): 345 (M+), 316, 147 and 141 (base)

EXAMPLE 20

Nuclear magnetic resonance spectrum δ: 8.3 to 7.2 (m, 11H), 3.94 (s, 2H), 3.53 (s, 2H), 2.48 (t, J=7Hz, 2H) and 1.24 (s, 9H)

Mass spectrum (m/e): 359 (M+), 316, 147 and 141 (base)

EXAMPLE 21

Nuclear magnetic resonance spectrum δ: 8.3 to 7.06 (m, 11H), 3.89 (s, 2H), 3.47 (s, 2H) and 2.15 (s, 3H)

Mass spectrum (m/e): 341 (M+), 339 (M+), 200, 198, 171, 169 and 141 (base)

EXAMPLE 22

Nuclear magnetic resonance spectrum δ: 8.3 to 7.0 (m, 11H), 3.90 (s, 2H), 3.54 (s, 2H), 3.80 (q, J=7.4Hz, 1H), 2.17 (s, 3H) and 1.22 (d, J=7.4Hz, 6H)

Mass spectrum (m/e): 303 (M+), 170, 155, 141 (base) and 133

EXAMPLE 23

Nuclear magnetic resonance spectrum δ: 8.3 to 7.0 (m, 11H), 3.88 (s, 2H), 3.54 (s, 2H), 2.59 (q, J=7Hz, 2H), 2.16 (s, 3H) and 1.19 (t, J=7Hz, 3H)

Mass spectrum (m/e): 289 (M+), 170, 148, 141 (base) and 119

EXAMPLE 24

Nuclear magnetic resonance spectrum δ: 8.3 to 7.0 (m, 11H), 3.88 (s, 2H), 3.55 (s, 2H), 2.58 (t, J=7Hz, 2H), 2.16 (s, 3H) and 1.9 to 1.2 (m, 4H)

Mass spectrum (m/e): 317 (M+), 176, 147 and 141 (base)

EXAMPLE 25

Nuclear magnetic resonance spectrum δ: 8.3 to 7.05 (m, 10H), 4.86 (s, 2H), 4.51 (s, 2H), 2.22 (s, 6H) and 2.16 (s, 3H)

Mass spectrum (m/e): 289 (M+), 170, 148, 141 (base) and 119

EXAMPLE 26

Nuclear magnetic resonance spectrum δ: 8.3 to 6.9 (m, 10H), 3.88 (s, 2H), 3.53 (s, 2H), 2.29 (s, 6H) and 2.19 (s, 3H)

Mass spectrum (m/e): 289 (M+), 170, 148, 141 (base) and 119

EXAMPLE 27

Nuclear magnetic resonance spectrum δ: 8.3 to 6.89 (m, 11H), 3.83 (s, 2H), 3.39 (s, 2H) and 2.10 (s, 3H)

Mass spectrum (m/e): 387 (M+), 260, 246, 217, 170 and 141

EXAMPLE 28

Nuclear magnetic resonance spectrum δ: 7.9 to 7.15 (m, 10H), 4.16 (s, 2H), 3.63 (s, 2H), 2.30 (s, 3H) and 1.31 (s, 9H)

Mass spectrum (m/e): 333 (M+), 176 (base), 153, 147, 128 and 120

EXAMPLE 29

Nuclear magnetic resonance spectrum δ: 8.0 to 7.2 (m, 9H), 3.74 (s, 2H), 3.54 (s, 2H), 2.21 (s, H) and 1.30 (s, 9H)

Mass spectrum (m/e): 147 (base), 148, 176 and 232 (M+)

EXAMPLE 30

Nuclear magnetic resonance spectrum δ: 8.0 to 7.2 (m, 9H), 3.76 (s, 2H), 3.55 (s, 2H), 2.54 (t, J=7.2Hz, 2H), 1.28 (s, 9H) and 1.07 (t, J=7.2Hz, 3H)

Mass spectrum (m/e): 147 (base), 148, 190, 322 and 337 (M+)

EXAMPLE 31

Nuclear magnetic resonance spectrum δ: 8.2 to 7.1 (m, 12H), 3.90 (s, 2H), 3.73 (s, 2H) and 2.20 (s, 3H)

Mass spectrum (m/e): 141, 147 (base), 148, 170, 176 and 317 (M+)

EXAMPLE 32

Nuclear magnetic resonance spectrum δ: 8.0 to 7.2 (m, 12H), 3.73 (s, 2H), 3.65 (s, 2H) and 2.20 (s, 3H)

Mass spectrum (m/e): 141, 142, 147 (base), 148, 170, 176 and 317 (M+)

EXAMPLE 33

Nuclear magnetic resonance spectrum δ: 7.9 to 7.4 (m, 8H), 3.72 (s, 2H), 2.52 (s, 3H), 2.20 (s, 2H) and 1.29 (s, 9H)

Mass spectrum (m/e): 161 (base), 162, 176, 190 and 337 (M+)

EXAMPLE 34

Nuclear magnetic resonance spectrum δ: 7.83 to 7.23 (m, 9H), 3.78 (s, 2H), 3.53 (s, 2H), 2.17 (s, 3H) and 1.32 (s, 9H)

Mass spectrum (m/e): 147 (base), 148, 176, 190 and 323 (M+)

EXAMPLE 37

Nuclear magnetic resonance spectrum δ: 7.64 (m, 8H), 3.73 (s, 2H), 3.57 (s, 2H), 2.15 (s, 3H) and 1.31 (s, 9H)

Mass spectrum (m/e): 147, 176 (base), 225, 227, 254, 256 401 (M+) and 403 (M³)

EXAMPLE 38

Nuclear magnetic resonance spectrum δ: 7.28 to 7.12 (m, 7H), 3.47 (s, 4H), 2.88 (t, J=7Hz, 4H), 2.17 (s, 3H), 2.02 (t, J=7Hz, 2H) and 1.30 (s, 9H)

Mass spectrum (m/e): 131 (base), 132, 147, 160, 176 and 307 (M+)

EXAMPLE 39

Nuclear magnetic resonance spectrum δ: 7.27 to 6.93 (m, 7H), 3.48, 3.45 (s, s, 4H), 2.95 to 2.62 (m, 4H), 2.13 (s, 3H), 1.88 to 1.67 (m, 4H) and 1.32 (s, 9H)

Mass spectrum (m/e): 129, 144 (base), 145, 147, 176, 178 and 321 (M+)

EXAMPLE 40

Nuclear magnetic resonance spectrum δ: 7.27 (s, 4H), 7.03 (s, 3H), 3.48, 3.45 (s, s, 4H), 2.9 to 2.6 (m, 4H), 2.16 (s, 3H), 1.88 to 1.67 (m, 4H) and 1.29 (s, 9H)

Mass spectrum (m/e): 139, 140, 141, 174, 176 (base) and 321 (M+)

EXAMPLE 41

Nuclear magnetic resonance spectrum δ: 8.15 to 6.83 (m,13H), 3.91 (s,2H), 3.81 (s,2H) and 2.19 (s,3H)

Mass spectrum (m/e): 137, 149 (base), 170, 188 and 327 (M+)

EXAMPLE 42

Nuclear magnetic resonance spectrum δ: 8.15 to 6.83 (m, 13H), 3.91 (s, 2H), 3.85 (s, 2H) and 2.19 (s, 3H)

Mass spectrum (m/e): 147, 154 (base), 176, 188 and 335 (M+)

EXAMPLE 43

Nuclear magnetic resonance spectrum δ: 8.36 to 6.87 (m, 13H), 3.90 (s, 2H), 3.71 (s, 2H) and 2.19 (s, 3H)

Mass spectrum (m/e): 137, 138, 149 (base), 170, 188 and 329 (M+)

EXAMPLE 44

Nuclear magnetic resonance spectrum δ: 8.3 to 7.1 (m, 13H), 3.94 (s, 2H), 3.87 (s, 2H) and 2.21 (s, 9H)

Mass spectrum (m/e): 137 (base), 138, 170, 175, 204 and 345 (M+)

EXAMPLE 45

Nuclear magnetic resonance spectrum δ: 8.35 to 7.2 (m, 13H), 3.84 (s, 2H), 3.66 (s, 2H) and 2.16 (s, 3H)

Mass spectrum (m/e): 137 (base), 138, 170, 175, 204 and 345 (M+)

EXAMPLE 46

Nuclear magnetic resonance spectrum δ: 8.32 to 7.11 (m, 13H), 3.92 (s, 2H), 3.83 (s, 2H) and 2.19 (s, 3H)

Mass spectrum (m/e): 137 (base), 138, 170, 219, 221, 248, 250, 389 and 391 (M+)

EXAMPLE 47

Nuclear magnetic resonance spectrum δ (in DMSO-$d_6$) 8.47 to 7.45 (m, 13H), 3.92 (s, 2H), 3.72 (s, 2H) and 2.16 (s, 3H)

Mass spectrum (m/e): 137 (base), 138, 170, 219, 221, 248, 250, 389 and 391 (M+)

EXAMPLE 48

Nuclear magnetic resonance spectrum δ: 8.2 to 7.1 (m, 13H), 3.90 (s, 4H), 2.61 (s, 3H) and 2.19 (s, 3H)

Mass spectrum (m/e): 137, 146 (base), 147, 170, 184 and 325 (M+)

EXAMPLE 49

Nuclear magnetic resonance spectrum δ: 8.44 to 7.3 (m, 13H), 3.95 (s, 2H), 3.74 (s, 2H), 2.66 (s, 3H) and 2.22 (s, 3H)

Mass spectrum (m/e): 137 (base), 138, 146 (base), 147, 170, 184 and 325 (M+)

EXAMPLE 50

Nuclear magnetic resonance spectrum δ: 8.57 to 7.23 (m, 13H), 3.85 (s, 2H), 3.66 (s, 2H) and 2.16 (s, 3H)

Mass spectrum (m/e): 137 (base), 138, 170, 186, 215 and 356 (M+)

EXAMPLE 51

Nuclear magnetic resonance spectrum δ: 8.55 to 7.3 (m, 14H), 4.40 (q, J=6.5Hz, 1H), 3.70, 3.63 (s, s, 2H), 2.21 (s, 3H) and 1.59 (d, J=6.5Hz, 3H)

Mass spectrum (m/e): 137 (base), 146, 162, 170, 184, 198, 310 and 325 (M+)

EXAMPLE 52

Nuclear magnetic resonance spectrum δ: 8.37 to 7.02 (m, 10H), 3.85 (s, 2H), 3.47 (s, 2H), 2.81 (t, J=7Hz, 4H), 2.13 (s, 3H) and 2.01 (t, J=7Hz, 2H)

Mass spectrum (m/e): 131, 137 (base), 150, 170 and 301 (M+)

EXAMPLE 53

Nuclear magnetic resonance spectrum δ: 8.0 to 6.8 (m, 10H), 3.73 (s, 2H), 3.36 (s, 2H), 2.9 to 2.5 (m, 4H), 2.07 (s, 3H) and 1.8 to 1.5 (s, 4H)

Mass spectrum (m/e): 129, 137, 139 (base), 172 and 315 (M+)

EXAMPLE 54

Nuclear magnetic resonance spectrum δ: 8.26 to 6.86 (m, 10H), 3.80 (s, 2H), 3.42 (s, 2H), 2.8 to 2.5 (m, 4H), 2.11 (s, 3H) and 1.9 to 1.6 (m, 4H)

Mass spectrum (m/e): 137 (base), 139, 170, 174 and 315 (M+)

EXAMPLE 55

Nuclear magnetic resonance spectrum δ: 8.09 to 6.94 (m, 10H), 3.91 (s, 2H), 3.54 (s, 2H), 2.9 to 2.5 (m, 4H), 2.51 (q, J=7Hz, 2H), 1.9 to 1.6 (m, 4H) and 1.05 (t, J=7Hz, 3H)

Mass spectrum (m/e): 137, 138 (base), 184, 186 and 329 (M+)

EXAMPLE 56

Nuclear magnetic resonance spectrum δ: 8.38 to 7.01 (m, 10H), 3.99 (s, 2H), 3.56 (s, 2H), 2.9 to 2.38 (m, 6H), 1.9 to 1.6 (m, 4H) and 1.07 (t, J=7Hz, 3H)

Mass spectrum (m/e): 137 (base), 139, 184, 188, 314 and 329 (M+)

EXAMPLE 57

Nuclear magnetic resonance spectrum δ: 8.12 (m, 10H), 3.94 (s, 2H), 3.56 (s, 2H), 3.0 to 2.33 (m, 6H), 1.9 to 1.28 (m, 6H) and 0.77 (t, J=7Hz, 3H)

Mass spectrum (m/e): 137 (base), 139, 198, 200, 314 and 343

EXAMPLE 58

Nuclear magnetic resonance spectrum δ: 8.35 to 7.03 (m, 10H), 3.98 (s, 2H), 3.57 (s, 2H), 2.9 to 2.34 (m, 6H), 1.9 to 1.3 (m, 6H) and 0.78 (t, J=7Hz, 3H)

Mass spectrum (m/e): 137 (base), 139, 314 and 343 (M+)

EXAMPLE 59

Nuclear magnetic resonance spectrum δ: 8.1 to 6.9 (m, 10H), 3.92 (s, 2H), 3.55 (s, 2H), 2.9 to 3.33 (m, 6H), 1.9 to 1.0 (m, 8H) and 0.76 (t, J=6Hz, 3H)

Mass spectrum (m/e): 137 (base), 139, 212, 214, 314 and 357 (M+)

EXAMPLE 60

Nuclear magnetic resonance spectrum δ: 8.35 to 7.04 (m, 10H), 3.95 (s, 2H), 3.54 (s, 2H), 2.9 to 2.37 (m, 6H), 1.9 to 1.0 (m, 8H) and 0.79 (t, J=6Hz, 3H)

Mass spectrum (m/e): 137 (base), 139, 314 and 357 (M+)

EXAMPLE 62

Nuclear magnetic resonance spectrum δ: 8.14 to 7.04 (m, 14H), 3.95 (s, 4H), 2.54 (q, J=7.5Hz, 2H) and 1.07 (t, J=7.5Hz, 3H)

Mass spectrum (m/e): 137 (base), 138, 184, 310 and 325 (M+)

EXAMPLE 63

Nuclear magnetic resonance spectrum δ: 8.37 to 7.15 (m, 14H), 3.90 (s, 2H), 3.60 (s, 2H), 2.49 (q, J=7Hz, 2H) and 1.00 (t, J=7Hz, 3H)

Mass spectrum (m/e): 1.37 (base), 138, 184, 310 and 325 (M+)

EXAMPLE 64

Nuclear magnetic resonance spectrum δ: 8.12 to 7.06 (m, 14H), 3.97 (s, 4H), 2.59 to 2.33 (m, 2H), 1.9 to 1.3 (m, 2H) and 0.71 (t, J=7Hz, 3H), Mass spectrum (m/e): 137 (base), 310 and 339 (M+)

EXAMPLE 65

Nuclear magnetic resonance spectrum δ: 8.36 to 7.2 (m, 14H), 3.98 (s, 2H), 3.68 (s, 2H), 2.50 (t, J=7Hz, 2H), 1.7 to 1.1 (m, 2H) and 0.75 (t, 3H)

Mass spectrum (m/e): 137 (base), 138, 198, 310 and 339 (M+)

EXAMPLE 66

Nuclear magnetic resonance spectrum δ: 8.11 to 7.0 (m, 14H), 3.93 (s, 4H), 2.46 (t, J=6.5Hz, 2H), 1.6 to 0.9 (m, 4H) and 0.69 (t, J=6Hz, 3H)

Mass spectrum (m/e): 137 (base), 138, 212, 310 and 353 (M+)

EXAMPLE 67

Nuclear magnetic resonance spectrum δ: 8.4 to 7.35 (m, 14H), 4.06 (s, 2H), 3.77 (s, 2H), 2.54 (t, J=7Hz, 2H), 1.8 to 0.9 (m, 4H) and 0.77 (t, J=6Hz, 3H)

Mass spectrum (m/e): 137 (base), 138, 212, 310 and 353 (M+)

EXAMPLE 68

Nuclear magnetic resonance spectrum δ: 8.44 to 7.2 (m, 13H), 4.02 (s, 2H), 3.91 (s, 2H) and 2.28 (s, 3H)

Mass spectrum (m/e): 138 (base), 170 and 312 (M+)

EXAMPLE 69

Nuclear magnetic resonance spectrum δ: 8.4 to 6.7 (m, 9H), 3.95 (s, 2H), 3.76 (s, 2H), 2.25 (s, 3H) and 1.33 (s, 9H)

Mass spectrum (m/e): 137, 141 (base), 144, 182, 190 and 323 (M+)

EXAMPLE 70

Nuclear magnetic resonance spectrum δ: 8.13 to 7.28 (m, 9H), 4.11 (s, 2H), 3.83 (s, 2H), 1.74 (broad s, 1H) and 1.29 (s, 9H)

Mass spectrum (m/e): 137 (base), 138, 141, 147, 151 and 303 (M+)

EXAMPLE 71

Nuclear magnetic resonance spectrum δ: 8.82 to 7.26 (m, 10H), 3.85 (s, 2H), 3.54 (s, 2H), 2.17 (s, 3H) and 1.27 (s, 9H)

Mass spectrum (m/e): 141 (base), 171, 176, 190 and 318 (M+)

EXAMPLE 72

To a mixture of 1.03 g of N-methyl-1-naphthylmethylamine, 0.7 g of sodium carbonate and 10 ml of dimethylformamide was added 1.3 g of 4-tert-pentylbenzyl chloride and was stirred at room temperature for 16 hours. The reaction mixture was poured into water and extracted with benzene, and the benzene solution was washed with water. After distilling away benzene, 1.5 ml of concentrated hydrochloric acid was added and then an excess of concentrated hydrochloric acid was removed. A small amount of acetone was added and 1.33 g of formed white crystal was filtrated. White crystal of N-(4-tert-pentylbenzyl)-N-methyl-1-naphthylmethylamine hydrochloride (Compound of Example 12) was obtained by recrystallization from acetone.

Melting point: 191° to 193° C.

Nuclear magnetic resonance spectrum δ: 8.3 to 7.3 (m, 11H), 3.88 (s, 2H), 3.54 (s, 2H), 2.17 (s, 3H), 1.61 (q, J=7.3Hz, 2H), 1.26 (s, 6H) 0.67 (t, J=7.3Hz, 3H)

Mass spectrum (m/e): 331 (M+), 190, 170, 155 and 141 (base)

EXAMPLE 73

A mixture of 3.43 g of N-methyl-naphthylmethylamine, 3.65 g of 4-tert-butylbenzyl chloride, 2.33 g of anhydrous sodium carbonate and 20 ml of dimethyl formamide was stirred at 50° C. for 16 hours. The reaction mixture was poured into water and extracted with benzene, and the benzene solution was washed with water. After distilling away benzene, 3 ml of concentrated hydrochloric acid was added at cooling. An excess of hydrochloric acid was removed under reduced pressure and a suitable amount of acetone was added. White crystal (5.9 g) was precipitated and was filtered. N-(4-tertbutylbenzyl)-N-methyl-lnaphthylmethylamine hydrochloride of white plate crystal (Compound of Example 1) was obtained by recrystallization from acetone/ethanol. Melting point: 210° to 212° C.

The procedures of Example 73 were repeated to give hydrochlorides of amine derivatives of Examples 1 to 71.

EXAMPLE 74

N-(4-Fluoro-1-naphthylmethyl)-N-methyl-4-tertbutylbenzamide (1.94 g) (Compound of Example 4) was obtained by the reaction of 1.14 g of N-Methyl-4-fluoro-1-naphthylmethylamine and 1.24 g of 4-tert-Butylbenzyl chloride.

EXAMPLE 75

N-4-tert-Butylbenzyl-N-methyl-1-(1-naphthyl)ethylamine (1.61 g) (Compound of Example 9) was obtained by the reaction of 1.11 g of N-Methyl-1-(1-naphthyl) ethylamine and 1.24 g of 4-tert-Butylbenzyl chloride.

EXAMPLE 76

N-4-Isopropylbenzyl-N-methyl-1-naphthylmethylamine (1.75 g) (Compound of Example 22) was obtained by the reaction of 1.03 g of N-Methyl-1-naphthylmethylamine and 0.99 g of 4-tert-Butylbenzyl chloride.

EXAMPLE 77

N-4-tert-Butylbenzyl-N-methyl-benzo[b]thienylmethylamine (1.78 g) (Compound of Example 29) was obtained by the reaction of 0.98 g of N-Methyl-3-benzo[b]thienylmethylamine and 1.24 g of 4-tertButylbenzyl chloride.

EXAMPLE 78

To a mixture of 0.48 g of lithium aluminum hydride and 10 ml of anhydrous diethyl ether was added dropwise a solution of 3.0 g of N-methyl-N-(1-naphthylmethyl)-4-isopropylbenzamide in 10 ml of anhydrous diethyl ether and the reaction mixture was refluxed for 24 hours. At cooling, water was added dropwise to decompose an excess of lithium aluminum hydride. The reaction mixture was further diluted with water and extracted with diethyl ether, and the ether solution was washed with water. After adding 1.5 ml of concentrated hydrochloric acid to the ether solution, the ether was distilled away under reduced pressure. A small amount of acetone was added and formed white crystal (1.5 g) was filtrated. White plate crystal of N-(4-isopropylbenzyl)N-methyl-1-naphthylmethylamine hydrochloride (Compound of Example 22) was obtained by recrystallization from aceton/ethanol.

Melting point: 195.5° to 197° C.

EXAMPLE 79

A mixture of 1.03 g of 1-naphthoic acid and 4.86 g of thionyl chloride was stirred at 50° C. for 2 hours. An excess of thionyl chloride was removed under reduced pressure to give 1-naphthoyl chloride. A solution of 1-naphthoyl chloride in 10 ml of benzene was added dropwise to mixture of 1.06 g of N-methyl-4-tertbutylbenzylamine, 2 ml of pyridine and 10 ml of dry benzene and was stirred for 5 hours. The resultant was poured into water and extracted with benzene, and the benzene solution was washed successively with 3% aqueous solution of sodium bicarbonate, 3% hydrochloric acid and water, and then dried over anhydrous sodium sulfate. Oily product (1.74 g, amide) was obtained by distilling away benzene and was crystallized by leaving as it was. Melting point: 106° to 108° C. (recrystallized from hexane/benzene)

A solution of 1.33 g of the above amide in 10 ml of ether was added dropwise to a mixture of 0.38 g of lithium aluminum hydride and 40 ml of anhydrous ether and was refluxed for 12 hours. After adding water dropwise to decompose an excess of lithium aluminum hydride, the resultant was extracted with ether and washed with water. To the ether solution was added 1 ml of concentrated hydrochloric acid. Solvent was distilled away under reduced pressure, a suitable amount of acetone was added and precipitated white crystal (1.3 g) was filtrated. N-(4-tert-Butylbenzyl)-N-methyl-1-naphtylmethylamine hydrochloride of white plate crystal (Compound of Example 1) was obtained by recrystallization from acetone/ethanol.

Melting point: 210° to 212 ° C.

EXAMPLE 80

N-4-tert-Butylbenzyl-N-methyl-4-fluoro-1-naphthamide (Compound of Example 4) was obtained by reacting N-4-tert-Butylbenzyl-N-methyl-4-fluoro-1-naphthamide.

EXAMPLE 81

N-Methyl-N-4-tert-pentylbenzyl-1-naphthylmethylamine (Compound of Example 12) was obtained by reacting N-Methyl-N-4-tert-pentylbenzyl-1-naphthamide.

EXAMPLE 82

N-4-tert-Butylbenzyl-N-methyl-3-benzo[b]thionylmethylamine (Compound of Example 29) was obtained by reacting N-4-tert-Butylbenzyl-N-methyl-3-benzo[b]thenamide.

The procedures of Examples 73 were repeated to give hydrochlorides of amine derivatives of Examples 1 to 71.

EXAMPLE 83

To a mixture of 6.07 g of lithium aluminum hydride and 80 ml of anhydrous diethyl ether was added dropwise a solution of 6.5 g of N-(4-tert-butylbenzyl)-N-methyl-2-ethoxycarboxy-1-naphthamide in 20 ml of anhydrous benzene and was refluxed for 3 hours. At cooling, water was added dropwise to decompose an excess of lithium aluminum hydride and the ether layer was separated. To the ether solution was added 3 ml of concentrated hydrochloric acid and an excess of hydrochloric acid was removed under reduced pressure. Then a small amount of acetone was added and formed white crystal (2.12 g) was filtrated.

White crystal of N-(4-tert-butylbenzyl)-N-methyl-2-hydroxy-1-naphthylmethylamine hydrochloride (Compound of Example 28) was obtained by recrystallization from methanol/acetone.

Melting point: 181° to 183° C.

The procedures of Examples 83 were repeated to give hydrochloride of amine derivatives of Examples 1 to 71.

EXAMPLE 84

A mixture of 1.06 g of 4-tert-butylbenzoic acid and 4.86 g of thionyl chloride was stirred for 2 hours at 50° C. An excess of thionyl chloride was distilled away under reduced pressure to give acid chloride, which was suspended into 10 ml of dry benzene and the suspension was added dropwise to a mixture of 1.03 g of N-methyl-1-naphthylmethylamine, 2 ml of pyridine and 10 ml of dry benzene. After stirring for 6 hours at room temperature, the reaction mixture was poured into water and extracted with benzene, and the benzene solution was washed successively with 3% aqueous solution of sodium bicarbonate, 3% hydrochloric acid and water and then dried over anhydrous sodium sulfate. Oily product (1.95 g, amide) was obtained by distilling away benzene.

A solution of the above amide in 20 ml of anhydrous ether was added drpwise to a mixture of 0.57 g of lithium aluminum hydride and 40 ml of anhydrous ether and refluxed for 12 hours.

After adding water dropwise to decompose an excess of lithium aluminum hydride, the resultant was extracted with ether and the ether solution was washed with water. At cooling, 2 ml of concentrated hydrochloric acid was added to the ether solution. Solvent was distilled away under reduced pressure, a suitable amount of acetone was added and precipitated white crystal (1.9 g) was filtered. N-(4-tertButylbenzyl)-N-methyl-1-naphthylmethylamine hydrochloride of white plate crystal (Compound of Example 1) was obtained by recrystallization from acetone/ethanol. Melting point: 210° to 212° C.

EXAMPLE 85

N-4-tert-Butylbenzyl-N-methyl-4-fluoro-1-naphthamide (Compound of Example 4) was obtained by reacting N-(4-Fluoro-1-naphthylmethyl)-N-methyl-4-tert-butylbenzamide.

EXAMPLE 86

N-4-tert-Butylbenzyl-N-methyl-1-(1-naphthyl)ethylamine (Compound of Example 9) was obtained by reacting N-Methyl-N-1-(1-naphtyl)ethyl-4-tert-butylbenzamide.

EXAMPLE 87

N-Methyl-N-4-tert-pentylbenzyl-1-naphthylmethylamine (Compound of Example 12) was obtained by reacting N-Methyl-N-1-naphtylmethyl-4-tert-pentylbenzylamide.

EXAMPLE 88

N-4-Isopropylbenzyl-N-methyl-1-naphthylmethylamide (Compound of Example 22) was obtained by reacting N-Methyl-N-1-naphthylmethyl-4-isopropylbenzamide.

EXAMPLE 89

N-4-tert-Butylbenzyl-N-methyl-3-benzo[b]thienylmethylamine (Compound of Example 29) was obtained by reacting N-3-Benzo[b]thienylmethyl-4-tert-butylbenzamide.

PREPARATION EXAMPLE 1 (LIQUID PREPARATION)

To 500 ml of ethanol was added to dissolve 50 g of macrogol 400 and 10 g of N-(4-tert-butylbenzyl)-N-methyl-1-naphthylmethylamine hydrochloride obtained in Example 1. To the solution was gradually added 400 g of purified water. To the resulting solution, ethanol was further added so as to become 1000 ml as a total amount.

PREPARATION EXAMPLE 2 (OINTMENT)

To a mixture of 400 g of white petrolatum, 180 g of cetanol, 50 g of sorbitan sesquioleate, 5 g of lauromacrogol and 1 g of propyl parahydroxybenzoate, which was kept on a water bath at 80° C., was added to dissolve 10 g of N-(4-tert-butylbenzyl)-N-methyl-1naphthylmethylamine hydrochloride obtained in Example 1. To 353 g of purified water was added 1 g of methyl parahydroxybenzoate and warmed to 80° C. The obtained solution was gradually added to the former solution and stirred thoroughly. Heating was stopped and the mixture was further stirred with cooling until it congealed.

PREPARATION EXAMPLE 3 (CREAM)

A mixture of 15 g of white petrolatum, 200 g of liquid paraffin, 50 g of stearyl alcohol, 40 g of glyceryl monostearate, 145 g of propylene glycol and 1 g of propyl parahydroxybenzoate was kept on a water bath at 80° C. to dissolve and thereto 10 g of N-(4-tert-butylbenzyl)-N-methyl-1-naphthylmethylamine hydrochloride obtained in Example 1 was added to dissolve. To 40 g of polyoxyl 40 stearate and 1 g of methyl parahydroxybenzoate was added 498 g of purified water and was kept at 80° C. to dissolve. The obtained solution was added to the former solution and was stirred thoroughly. After stirring, the resultant was further stirred thoroughly while cooling with chilled water until it congealed.

TEST EXAMPLE 1

In vitro antifungal activity test

The antifungal activity of the compound of the present invention against Trichophyton metagrophytes, Trichophyton interdigitale and Trichophyton rubrum was tested employing Sabouraud's agar medium.

Each test compound shown in Table 4 was dissolved into 1 ml of ethanol and thereto distilled water was added to adjust to the concentration of 1000 μg/ml. In this way twofold dilution series was made, 1 ml of which was respectively taken into shale and therewith 9 ml of Sabouraud's agar medium was mixed to form plate medium.

In this plate medium was implanted 0.005 ml of each test fungus at $2 \times 10^6$ spores/ml by the microplanter MIP-2 (Sakuma Seisakusho Co., Ltd.) and was incubated at 27° C. for 7 days. The results were shown in Table 2 as the minimal growth-inhibitory concentration (MIC, μg/ml).

TABLE 2

| Test compound | Test fungus | | |
|---|---|---|---|
| | (a) | (b) | (c) |
| Example 1 | 0.0125 | 0.006 | 0.003 |
| Example 2 | 0.2 | 0.1 | 0.1 |
| Example 3 | 0.1 | 0.05 | 0.025 |
| Example 4 | 0.025 | 0.006 | 0.006 |
| Example 5 | 0.1 | 0.1 | 0.025 |
| Example 6 | 0.2 | 0.2 | 0.05 |
| Example 7 | 0.78 | 0.39 | 0.39 |
| Example 8 | 0.1 | 0.05 | 0.025 |
| Example 9 | 0.025 | 0.025 | 0.003 |
| Example 10 | 1.56 | 1.56 | 0.39 |
| Example 12 | 0.0125 | 0.0125 | 0.006 |
| Example 13 | 25 | 25 | 12.5 |
| Example 14 | 12.5 | 6.25 | 6.25 |
| Example 15 | 0.78 | 3.13 | 0.39 |
| Example 16 | 3.13 | 1.56 | 1.56 |
| Example 17 | 1.56 | 1.56 | 1.56 |
| Example 18 | 0.1 | 0.05 | 0.006 |
| Example 19 | 0.78 | 0.2 | 0.2 |
| Example 20 | 6.25 | 6.25 | 3.13 |
| Example 22 | 0.025 | 0.1 | 0.0125 |
| Example 23 | 0.1 | 0.2 | 0.1 |
| Example 24 | 0.1 | 0.2 | 0.1 |
| Example 25 | 0.78 | 0.78 | 0.39 |
| Example 26 | 12.5 | 12.5 | 6.25 |
| Example 28 | 25 | 12.5 | 6.25 |
| Example 29 | 0.05 | | 0.05 |
| Example 30 | 0.78 | | 0.78 |
| Example 33 | 0.2 | | 0.1 |
| Example 34 | 0.025 | | 0.025 |
| Example 35 | 0.78 | | 0.78 |
| Example 39 | 0.39 | | 0.39 |
| Example 43 | 0.2 | | 0.2 |
| Example 49 | 0.39 | | 0.39 |
| Example 51 | 0.39 | | 0.2 |
| Example 54 | 0.1 | | 0.1 |
| Example 56 | 0.2 | | 0.2 |
| Example 63 | 0.39 | | 0.1 |
| Example 69 | 0.05 | | 0.025 |

(a) Trichophyton mentagrophytes
(b) Trichophyton interdigitale
(c) Trichophyton rubrum As the result of Test, all test compounds shown in Table 2 were proved to have antifungal activity.

TEST EXAMPLE 2

Test on treatment of trichophytosis

In the back of male Hartley guinea pig weighing 600 to 700 g, four portions were unhaired in an area of 4 cm² respectively and rubbed lightly with sandpaper, to which the second generation of Trichophyton mentagrophytes incubated inversely from another guinea pig was infected at $1 \times 10^5$ spores per portion. The test compounds obtained in Example 1 was dissolved in ethanol and 0.2 ml of the resultant 0.1% solution was applied to the infected portions once in a day for ten days since 48 hours after the infection. Test animal was killed 2 days after the last treatment and 10 tissue specimens from each infected portions were placed on Sabouraud's plates containing cycloheximide and kanamycin, which were incubated at 27° C. for 7 days. After incubation, existence of fungi was observed and inhibitory ratio calculated according to the following equation showed high value of 82%.

inhibitory ratio = {1 − (number of tissue specimens found fungi/number of tissue specimens incubated inversely)} × 100

TEST EXAMPLE 3

Side effect test

Two portions in the back of male Hartley guinea pig weighing 600 to 700 g were unhaired in an area of 4 cm² respectively in order to examine side effects of the test compounds. The next day unhaired portions were lightly rubbed with sandpaper. The test compounds obtained in Example 1 was dissolved in ethanol and 0.2 ml/day of the resultant 0.5% solution was applied to one of the unhaired portions, while 0.2 ml/day of only ethanol was applied to the other portions, once in a day for ten days respectively.

As the result of test, side effects such as, for instance, erythema and papula were not observed.

What we claim is:

1. An amine derivative represented by formula (I):

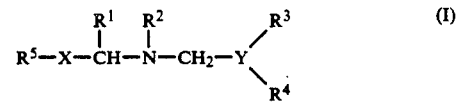

wherein X is 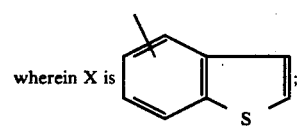;

Y is 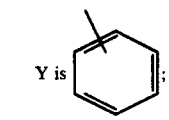;

$R^1$ is hydrogen atom or an alkyl group of 1 to 6 carbon atoms;
$R^2$ is hydrogen atom or an alkyl group of 1 to 6 carbon atoms;

$R^3$ is hydrogen atom or an alkyl group of 1 to 6 carbon atoms;

$R^4$ is hydrogen atom, an alkyl group of 1 to 10 carbon atoms, a cycloalkyl group of 3 to 7 carbon atoms or a halogenated alkyl group;

$R^5$ is hydrogen atom, an alkyl group of 1 to 6 carbon atoms, a halogen atom or a nitro group, wherein $R^5$ is attached to an arbitrary position of X, and $R^3$ or $R^4$ is attached to an arbitrary position of Y.

2. A fungicide composition containing an amine derivative represented by formula (I):

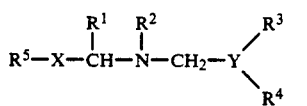

(I)

wherein X is 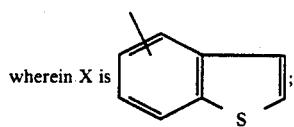;

Y is 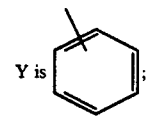;

$R^1$ is hydrogen atom or an alkyl group of 1 to 6 carbon atoms;
$R^2$ is hydrogen atom or an alkyl group of 1 to 6 carbon atoms;
$R^3$ is hydrogen atom or an alkyl group of 1 to 6 carbon atoms;
$R^4$ is hydrogen atom, an alkyl group of 1 to 10 carbon atoms, a cycloalkyl group of 3 to 7 carbon atoms or a halogenated alkyl group;
$R^5$ is hydrogen atom, an alkyl group of 1 to 6 carbon atoms, a halogen atom or a nitro group,
wherein $R^5$ is attached to an arbitrary position of X, and $R^3$ or $R^4$ is attached to an arbitrary position of Y.

* * * * *